(12) United States Patent
Grez et al.

(10) Patent No.: US 8,328,452 B2
(45) Date of Patent: Dec. 11, 2012

(54) POWER TOOTHBRUSH USING A SHEAR THICKENING FLUID

(75) Inventors: Joseph W. Grez, North Bend, WA (US); Michiel Allan Aurelius Schallig, Drachten (NL)

(73) Assignee: Koninklijke Philips Electronics N.A., Eindhoven (NL)

( * ) Notice: Subject to any disclaimer, the term of this patent is extended or adjusted under 35 U.S.C. 154(b) by 903 days.

(21) Appl. No.: 11/722,489

(22) PCT Filed: Dec. 21, 2005

(86) PCT No.: PCT/IB2005/054364
§ 371 (c)(1),
(2), (4) Date: Oct. 19, 2009

(87) PCT Pub. No.: WO2006/067759
PCT Pub. Date: Jun. 29, 2006

(65) Prior Publication Data
US 2010/0310301 A1 Dec. 9, 2010

Related U.S. Application Data

(60) Provisional application No. 60/638,228, filed on Dec. 22, 2004.

(51) Int. Cl.
*A46B 17/04* (2006.01)

(52) U.S. Cl. ........ 401/270; 401/268; 15/22.1; 15/167.1; 433/119

(58) Field of Classification Search .................. 401/268, 401/270; 15/22.1, 167.1; 433/216, 118, 433/119
See application file for complete search history.

(56) References Cited

U.S. PATENT DOCUMENTS

| | | | |
|---|---|---|---|
| 5,378,153 A | 1/1995 | Giuliani | |
| 6,202,241 B1 | 3/2001 | Hassell | |
| 7,020,928 B2 * | 4/2006 | Hohlbein | 15/167.1 |
| 7,049,790 B2 * | 5/2006 | Pfenniger et al. | 320/114 |
| 7,430,780 B2 * | 10/2008 | Moskovich et al. | 15/167.1 |
| 7,703,163 B2 * | 4/2010 | Jimenez et al. | 15/22.1 |

* cited by examiner

*Primary Examiner* — Steven J Ganey

(57) ABSTRACT

The combination of a power toothbrush and an oral fluid, in which the oral fluid has the characteristic of changing viscosity, depending upon the action of a workpiece element portion, such as a flexible membrane, of the power toothbrush. The power toothbrush has two operating conditions. In one condition, the membrane moves toward and away from the teeth at a speed such that the fluid is liquid and flows easily to and around the teeth, including the interproximal regions. In the second condition, the membrane is moved at a significantly higher speed, in response to which the viscosity of the fluid increases substantially, having a shear rate at least as great as necessary to remove biofilm from the teeth.

7 Claims, 3 Drawing Sheets

POWER TOOTHBRUSH USING A SHEAR THICKENING FLUID

CROSS REFERENCE TO RELATED APPLICATION

This application claims the benefit of U.S. provisional application Ser. No. 60/638,228 filed 22 Dec. 2004, which is incorporated herein by reference.

This invention relates generally to power toothbrushes, and more specifically to a combination of a power toothbrush and a fluid used with the power toothbrush which changes viscosity in response to operation of the power toothbrush.

In general, power toothbrushes for cleaning teeth, including removal of plaque, are well known. Typically, power toothbrushes rely on a set of bristles which are attached to a bristle mounting plate, which in turn is moved by a driver mechanism to scrub the surfaces of teeth. Various known bristle configurations produce different scrubbing effects on the exposed surfaces of the teeth, and to some small extent reach between the teeth interproximately or just under the gum line. However, such toothbrushes, which rely on scrubbing action of the bristles for actual cleaning, typically require some amount of pressure to be exerted by the user against the teeth, to accommodate differences in the various shapes and spacing of the teeth and to effectively clean the teeth. Such pressure, however, often results in an abrasion effect, including damage to both the soft and hard tissues in the mouth. This is, of course, undesirable.

In addition to a scrubbing effect, some power toothbrushes operate in a manner to produce a fluid movement in the mouth, particularly when the velocity of the bristles is relatively high, which in turn produces a cleansing effect on any biofilm plaque present on the teeth. Instead of just a scrubbing action, those toothbrushes produce a shear action, which removes surface portions of the biofilm, including biofilm in places where the scrubbing effect is unable to reach, such as interproximately between the teeth and under the gum line. This cleansing effect, which occurs with sonic (acoustic) frequency toothbrushes operating in an oral fluid, takes time and often does not produce optimum cleansing effects. However, the use of this acoustic-type cleaning action is still desirable, since it has very little, if any, abrasion effects, and can reach farther into dental spaces than bristles.

Accordingly, it would be desirable to have a toothbrush with action which has little abrasion, but cleans biofilm effectively from the teeth surfaces.

Accordingly, the present invention includes a power toothbrush/oral fluid combination for removing biofilm from teeth, comprising: an oral fluid having the characteristic of changing viscosity upon an increase in velocity of operation of a power toothbrush workpiece element; and a power toothbrush having a driving assembly for a workpiece element, wherein the driving assembly and the oral fluid have two operating conditions; in one condition, the driving assembly operates such that the oral fluid flows readily to and around the teeth in a liquid state; and in the other condition, the driving assembly and the workpiece operate at a sufficiently high velocity, that the viscosity of the fluid increases substantially, producing in operation of the oral fluid/power toothbrush combination a shear rate approximately at least as great as the threshold at which biofilm is removed from the teeth.

Figure 1:
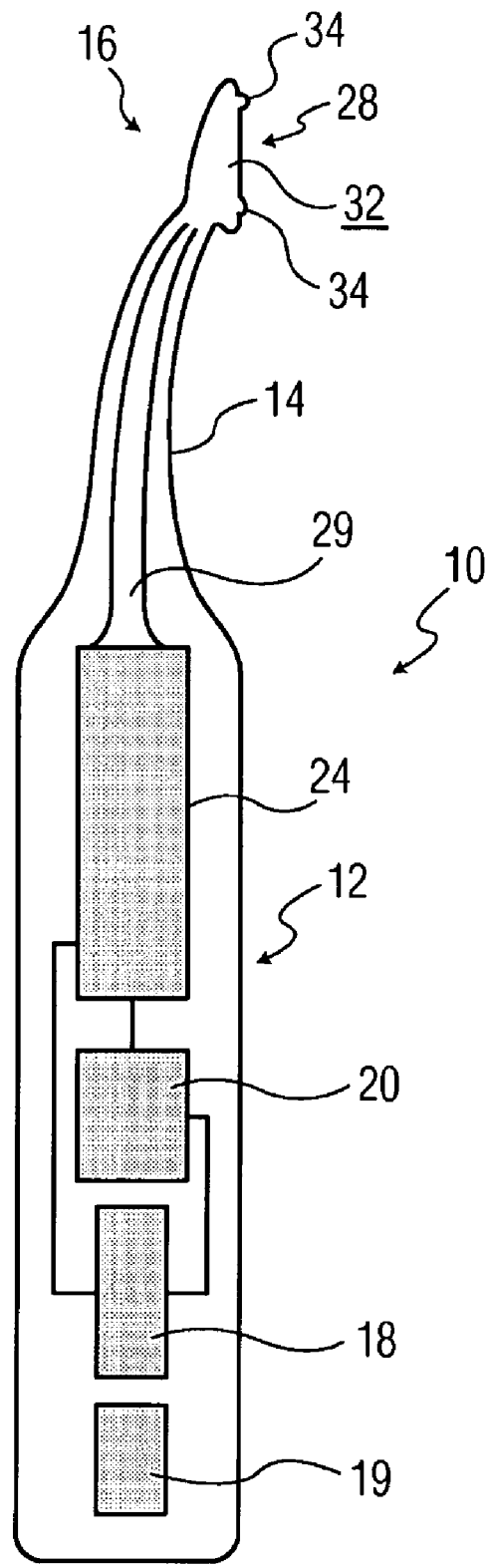
FIG. 1 is a perspective view of a power toothbrush which is part of the combination of the present invention.

FIG. 1 shows a power toothbrush portion of the combination of the present invention, generally at 10. The power toothbrush includes a handle portion 12, a stem portion 14 and a head portion 16. The combination of stem 14 and head 16 is referred to as a brushhead assembly. In handle 12 is located a conventional rechargeable battery 18 and a charging coil 19 to periodically charge the battery 18. Also in handle 12 is a control circuit 20 which in combination with the battery controls and powers an acoustic drive system 24. There can be various embodiments of the acoustic drive system 24, including one which is similar to an audio speaker system which produces acoustic wave action. Other possibilities include a piston drive system or the combination of a coil, a driven member and a vibrating surface. It should be understood, however, that the present invention is not limited to a particular acoustic drive system.

The drive system 24 produces an action by acoustic member workpiece 28. An acoustic transmission line 29 connects the drive system to the acoustic member 28. The acoustic member 28 may be a membrane or diaphragm made from flexible material, such as rubber or other similar material. It could also be a paddle or a bristle arrangement which does not make scrubbing contact with the teeth.

The acoustic member in essence replaces the more familiar conventional toothbrush bristles on a toothbrush. In operation, generally, it moves in and out, toward and away from the teeth, as shown by the arrows in FIG. 2A. It could also move tangentially relative to the teeth. The frequency of the action of the acoustic member will typically be in the range of 20-500 Hz, with 50-300 Hz being preferred. The member, which preferably is a membrane element, may be made from various materials and can have various configurations. It must, however, have a surface or surfaces which can act on a fluid over generally the dimensions of the brushhead. The configuration and particular material described herein, however, do not limit the present invention. Other possibilities include ribbed plungers, rotating discs and pistons.

The acoustic transmission line 29, connecting the acoustic drive system 24 with the driven member, e.g. membrane 28, extends through stem portion 14 of the toothbrush. The transmission line 29 can take various forms. It can be a fluid-filled tube, an air-filled tube or an actuator arm which transmits energy from drive system 24 to the acoustic member 28. The fluid in the transmission line could be a conditioned oil or a natural oil, or it could also be a water-based fluid. Additives could be used to prevent bacterial growth.

In operation, transmission line 29 transmits acoustic energy produced by the drive assembly 24 to the head portion 16 of the toothbrush and specifically the acoustic member 28 or similar member, such as a membrane in the preferred embodiment. In operation, acoustic member 28 is driven in and out by the acoustic drive energy transmitted through transmission line 29. The member 28 will typically move toward and away from the teeth, but may move in other directions. In the embodiment shown, the acoustic member 28 is generally rectangular, approximately 3 mm by 10 mm, although different configurations can be used. The member 28 moves between a concave configuration and a straighter or even convex configuration.

In operation, the front facing portion 32 of the member will move between 0.5 mm and 5 mm, depending upon the particular drive system used. The membrane structure of FIG. 1 also includes a stand-off rib 34 which extends around the periphery of the membrane. Rib 34 contacts the surfaces of the teeth and acts as a fluid boundary, so that the action of the membrane can exert significant pressure on the fluid between the membrane and the teeth.

During times when the membrane 28 is either not moving or moving very slowly, the oral fluid used with the toothbrush as part of the present combination system is liquid, flowing easily around and between the teeth and under the gum line. When the actuator (membrane) increases to a high speed (velocity range of 0.5-25 m/s), the viscosity of the fluid increases dramatically, as discussed in more detail below, to the point where the fluid has a viscosity similar to that of the plaque on the teeth, so that the fluid produces a highly effective shearing effect on the biofilms (plaque) present on the teeth.

Fluids which exhibit this characteristic of increasing viscosity due to a high speed motion of an actuating or directing member are referred to as "shear thickening" fluids. Among them are various combinations of starches, including corn starch and water, as well as certain existing toothpastes and water, potato starches and selected powders. Ratios of 1:1 to 1:3 starch to water have been effective as shear thickening fluids. Other shear thickening fluids can be used. Shear thickening has been shown to occur with fluid volumes suitable for in-mouth conditions, 0.5 ml or less. The viscosity of the fluid will increase dramatically by forces produced by the high speed motion of the actuating member, such as a flexible membrane. A frequency of 260 Hz with the range of movement discussed above has been shown to produce good results.

When the actuator (membrane) is at rest or in a very slow action (the first operating condition), the viscosity of such a fluid will be below 100 Pa. sec., while at an operative shear thickening motion, the viscosity can be increased by several orders of magnitude, producing a shear rate of up to 3000 Pa. or higher. Biofilms require a shear rate of between 100 and 1000 Pa for removal. The shear rate of the fluid when it is in its highly viscous state must be great enough to remove biofilm.

Figure 2A:
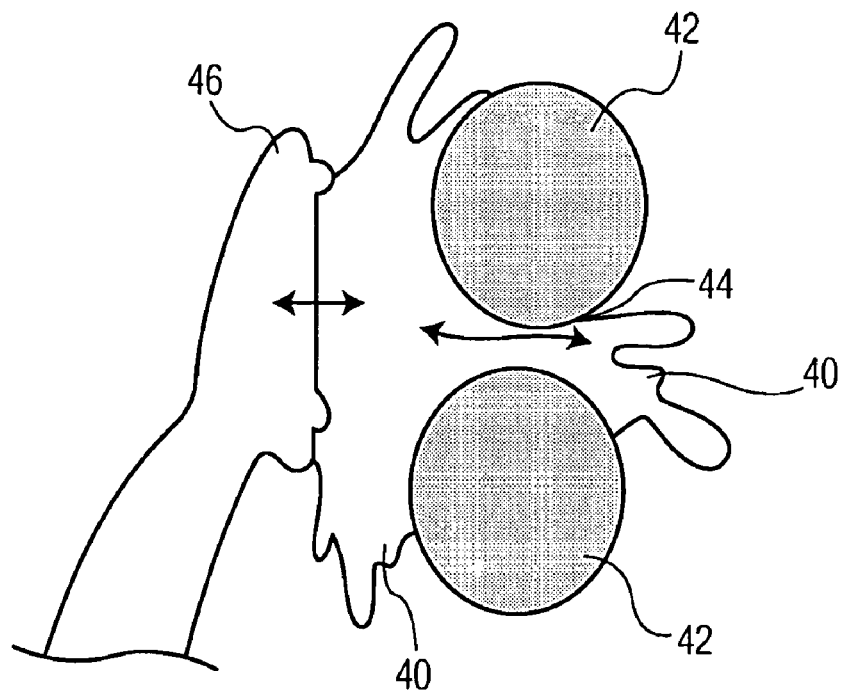
FIGS. 2A and 2B show a portion of the power toothbrush and the movement of fluid relative to the teeth produced by the combination of the present invention.
Figure 2B:
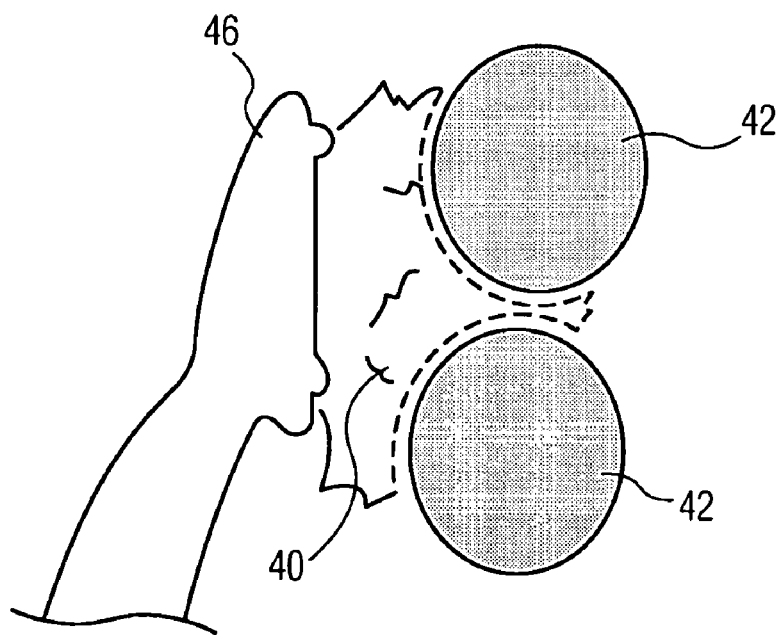

FIGS. 2A and 2B show action of the shear thickening fluid against the teeth during the "slow" or stopped actuator phase and the "fast" actuator phase, respectively. In the slow phase, the fluid 40 moves around the teeth 42-42 and into the space 44 between the teeth, as well as into the space between the gums and the teeth (not shown). In the slow speed or stopped actuator mode, the fluid is very liquid, with low viscosity, as pointed out above, and hence has a low shear.

FIG. 2B illustrates the fast mode of the actuator, in which the membrane 46 is moving at a frequency of 260 Hz in the embodiment shown. The viscosity of the shear thickening fluid 40 increases substantially (several orders of magnitude) when the actuator is moving at this high frequency, significantly above that of water or a normal toothpaste. The movement of the now high viscosity fluid 40 by the fast-moving actuator 46 results in a transmission of force to targeted spaces, with the high viscosity fluid acting with great effect on the biofilms present on the teeth, shearing them from the teeth. Virtually the entire biofilm layer is affected by such action, instead of merely a small upper portion thereof. Effective cleaning results. There is no damage to the tissues caused by scrubbing action, as it is the shear action of the moving, high viscosity fluid which produces the removal of the biofilms, without scrubbing.

Since the fluid moves into the interproximal spaces and beneath the gum line when it is in its low viscosity mode, the action of the fluid when it is in its high viscosity mode (when the membrane is in its fast mode) produces effective biofilm cleaning of those interproximal and gum line spaces, in addition to such cleaning of the exposed surfaces of the teeth.

Figure 3A:
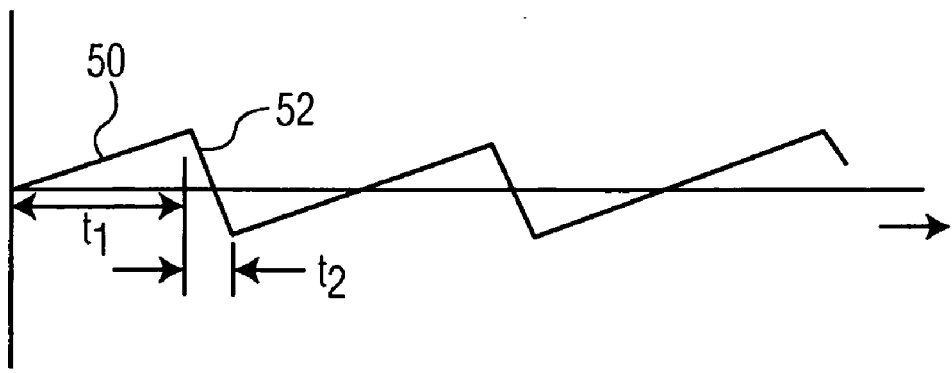
FIGS. 3A, 3B and 3C show three different types of movement of the membrane portion of the toothbrush of the present combination.
Figure 3B:
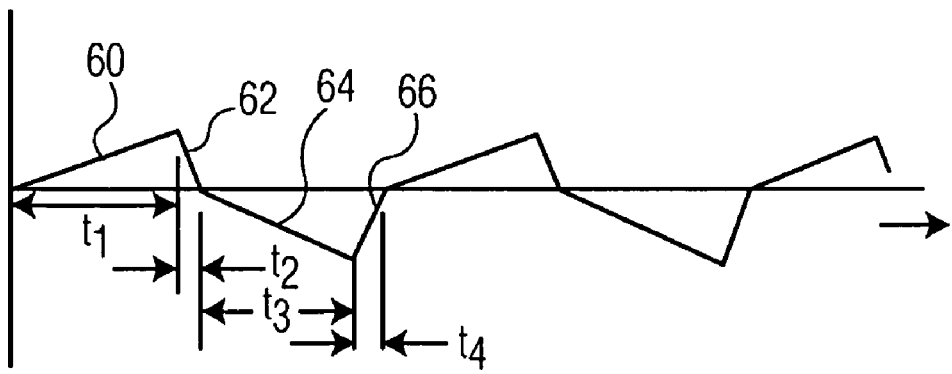
Figure 3C:
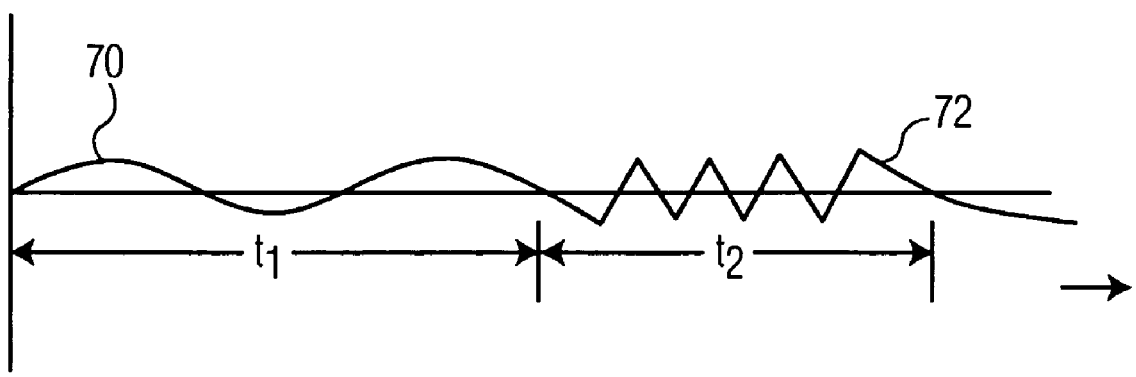

FIGS. 3A, 3B and 3C show three different possible actions of a membrane actuator (slow and fast phases). In FIG. 3A, the membrane deflection changes in a direction toward the teeth linearly over time at a rather slow pace during a first phase 50, in which the fluid flows around the teeth and into the crevices (interproximal spaces), followed by a fast movement in the opposing direction, away from the teeth, during a second phase 52, for cleansing action. Time $t_1$ could be approximately 8 ms., while time $t_2$ could be approximately 2 ms. The action of phases 50 and 52 are then repeated successively, producing an alternating fluid flow/biofilm cleaning process for the teeth, including interproximately and beneath the gum line.

FIG. 3B shows a second possible slow phase-fast phase membrane action, in which a linear movement of the membrane actuation is slow in a direction toward the teeth during a first phase 60 (fluid flow over time $t_1$), followed by a fast movement away from the teeth during a second phase 62 (biofilm cleaning) over time $t_2$, followed by a further movement in the same direction away from the teeth during a third phase 64 (fluid flow) over time $t_3$ and a final fast movement in the opposing direction back toward the teeth during a fourth phase 66 (biofilm cleaning) over time $t_4$. This pattern of slow/fast membrane movement repeats itself over time to give the desired cleansing action.

FIG. 3C shows an oscillating motion of the membrane during a slow phase (70) for flow during time $t_1$ and a triangle drive motion during a fast phase 72 for fluid flow during time $t_2$.

The examples of the actuation pattern of the membrane of FIGS. 3A, 3B and 3C are representative only. Other actuation patterns can be readily determined and implemented by one skilled in the art. It is important, however, that slow phase or mode for the power toothbrush, producing liquid flow of the dentifrice around the teeth, be followed by fast movement to produce a shear thickening of the oral fluid, i.e. a substantial increase in viscosity, which in turn results in a shearing effect on the biofilm on the teeth. The advantage of the present system, using a combination of an actuator, such as a flexible membrane, with a shear thickening fluid, is that a high level of effective cleaning, including interproximately, can be accomplished quickly without any of the detrimental effects such as discomfort or tissue damage caused by bristle scrubbing action.

Although a preferred embodiment of the invention has been disclosed for purposes of illustration, it should be understood that various changes, modifications and substitutions may be incorporated in the embodiment without departing from the spirit of the invention which is defined by the claims which follow.

The invention claimed is:

1. A power toothbrush/oral fluid combination for removing biofilm from teeth, comprising:
    an oral fluid having the characteristic of changing viscosity upon an increase in frequency of operation of a power toothbrush workpiece element; and
    a power toothbrush having a driving assembly for a workpiece element, wherein the driving assembly and the oral fluid have two operating modes, in a first mode, the driving assembly operates at such a low frequency that the oral fluid has a low viscosity and flows readily to and around the teeth in a liquid state; and in a second mode, the driving assembly and the workpiece element operate at a sufficiently high frequency that the viscosity of the oral fluid increases substantially, producing in operation of the power toothbrush/oral fluid combination a shear rate for the fluid around the teeth as a result of the first mode of operation approximately at least as great as the threshold at which biofilm is removed from the teeth.

2. The combination of claim 1, wherein in the second mode, the oral fluid has a viscosity which results in a shear rate approximately equal to that for removing biofilm from teeth.

3. The combination of claim 1, wherein in the second mode of operation, the workpiece element moves at a frequency within the range of 15-500 Hz.

4. The combination of claim 1, wherein the workpiece element includes a boundary element which extends away from a workpiece element surface, acting as a fluid boundary.

5. The combination of claim 1, wherein the workpiece element is a flexible membrane, which in operation moves toward and away from the teeth.

6. The combination of claim 1, wherein the workpiece element is a flexible member, which in operation moves tangentially with respect to the surface of the teeth.

7. The combination of claim 1, wherein in the second mode, the oral fluid has a viscosity which is at least as great as the threshold shear rate for removal of interproximal biofilm and wherein the power toothbrush is otherwise adapted for removal of interproximal biofilm.

* * * * *